United States Patent [19]

Arai

[11] 4,319,034
[45] Mar. 9, 1982

[54] NOVEL ORGANOCYCLOTETRASILOXANES

[75] Inventor: Masatoshi Arai, Annaka, Japan

[73] Assignee: Shin-Etsu Chemical Co., Ltd., Tokyo, Japan

[21] Appl. No.: 218,122

[22] Filed: Dec. 19, 1980

[30] Foreign Application Priority Data

Dec. 24, 1979 [JP] Japan .................................. 54-168924

[51] Int. Cl.³ .............................................. C07F 7/10
[52] U.S. Cl. ...................................... 556/425; 556/422
[58] Field of Search ................................. 556/425, 422

[56] References Cited

U.S. PATENT DOCUMENTS 2,942,019  6/1960  Pike et al. ...................... 556/425 X
3,022,270  2/1962  Lisanke ........................... 556/425 X
3,484,471  12/1969  Murphy ............................... 556/422

FOREIGN PATENT DOCUMENTS 882057 11/1961 United Kingdom ................ 556/422

*Primary Examiner*—Paul F. Shaver
*Attorney, Agent, or Firm*—Toren, McGeady & Stanger

[57] ABSTRACT

The invention provides a novel class of cyclic organotetrasiloxanes represented by the general formula

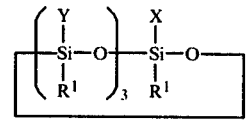

in which $R^1$ is a monovalent hydrocarbon group, e.g. methyl, Y is a hydrogen atom or a dialkylaminoxy group and X is a hydrocarbylideneiminopropyl group.

11 Claims, 3 Drawing Figures

NOVEL ORGANOCYCLOTETRASILOXANES

BACKGROUND OF THE INVENTION

The present invention relates to a novel class of organocyclotetrasiloxanes hitherto not known or not described in any prior art literatures useful as an intermediate compound in the synthesis of various kinds of organosilicon compounds or as a crosslinking agent in the curing of vinyl- or hydroxy-containing organopolysiloxanes as the base ingredient in silicone rubbers or other curable silicone materials. The invention also relates to the method for the preparation of the above mentioned organocyclotetrasiloxanes.

SUMMARY OF THE INVENTION

The novel organocyclotetrasiloxanes of the invention are represented by the general formula

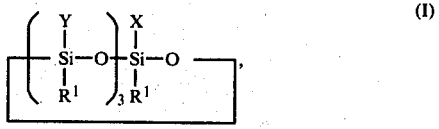

in which Y is a hydrogen atom or a disubstituted aminoxy group of the formula $R^2{}_2N-O-$, $R^2$ being a monovalent hydrocarbon group having from 1 to 6 carbon atoms, X is a hydrocarbylideneimino-substituted propyl group of the formula

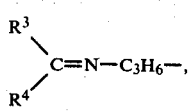

$R^3$ being a monovalent hydrocarbon group free from aliphatic unsaturation having from 1 to 8 carbon atoms, or of the formula

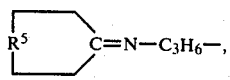

$R^5$ being a divalent hydrocarbon group free from aliphatic unsaturation having from 4 to 8 carbon atoms, and $R^1$ is a monovalent hydrocarbon group having from 1 to 8 carbon atoms.

The inventive siloxane compounds in which Y is a hydrogen atom are prepared by the addition reaction of a 1,3,5,7-tetraorganocyclotetrasiloxane with a controlled amount of an allylimine compound catalytically accelerated by a platinum compound.

The siloxane compounds in which Y is a disubstituted aminoxy group can be obtained from the corresponding cyclosiloxane of the formula (I) in which Y is a hydrogen atom by the dehydrogenation reaction with a disubstituted hydroxylamine compound.

DETAILED DESCRIPTION OF THE PREFERRED EMBODIMENTS

Figure 1:
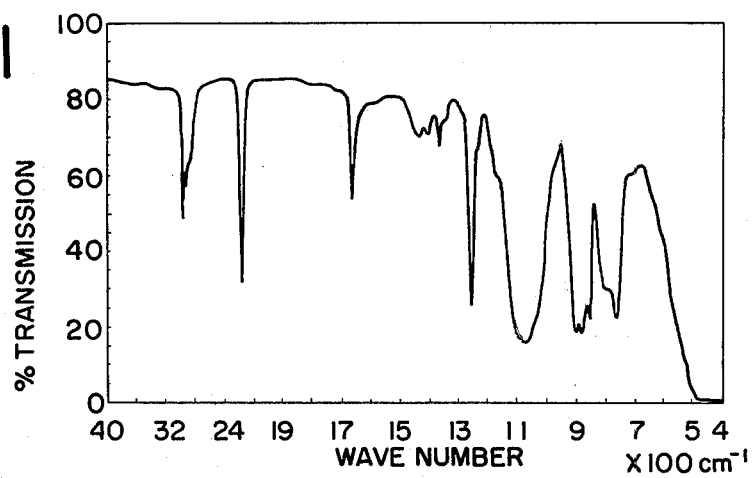
FIGS. 1 to 3 are each an infrared absorption spectrum of the product compound obtained in Example 1, Example 2 and Example 5, respectively.

In the above given general formula (I), the symbol $R^1$ denotes a monovalent hydrocarbon group having 1 to 8 carbon atoms as exemplified by alkyl groups such as methyl, ethyl, propyl, butyl, hexyl and octyl groups, aryl groups such as phenyl and tolyl groups and aralkyl groups such as benzyl group as well as those substituted hydrocarbon groups with chlorine or other atoms or cyano or other groups in place of part or all of the hydrogen atoms in the above named hydrocarbon groups.

When Y in the formula (I) is a disubstituted aminoxy group of the formula $R^2{}_2N-O-$, $R^2$ is a monovalent hydrocarbon group having from 1 to 6 carbon atoms as exemplified by alkyl groups such as methyl, ethyl, propyl, butyl and hexyl groups and phenyl groups.

The monovalent hydrocarbon group denoted by $R^3$ or $R^4$ in the formula for the group X has from 1 to 8 carbon atoms and is free from aliphatic unsaturation as exemplified by the same groups as $R^1$ above whereas the divalent hydrocarbon group denoted by $R^5$ has also from 4 to 8 carbon atoms and is free from aliphatic unsaturation as exemplified by tetramethylene, pentamethylene and heptamethylene groups to form a 5-, 6- or 8-membered ring, respectively, jointly with the carbon atom bonded to the nitrogen atom.

Several of the particular examples of the groups denoted by X are as follows, in which, and hereinafter, the symbols Me, Et, Pr, Bu, Vi and Ph each denote methyl, ethyl, propyl, butyl, vinyl and phenyl groups, respectively:

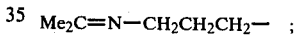

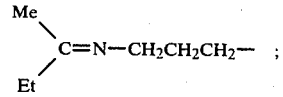

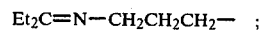

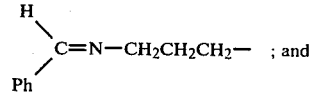

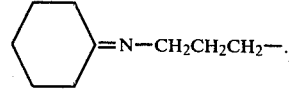

The inventive organocyclotetrasiloxane of the general formula (I) can be readily synthesized in a high yield by the addition reaction of a corresponding 1,3,5,7-tetraorganocyclotetrasiloxane and a controlled amount of an allylimine compound of the formula

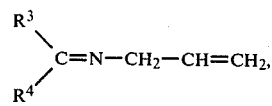

where $R^3$ and $R^4$ each have the same meaning as defined above, in the presence of a catalyst such as a platinum compound, preferably, under a nitrogen atmosphere. The allylimine compound of the above given formula is obtained by a known method (see, for example, Journal of the Organic Chemistry, volume 19 (1954), page 1054)

from an aldehyde or ketone compound and an amine compound by the condensation reaction in the presence of an acid catalyst.

The molar ratio of the reactants in the above mentioned addition reaction between the cyclotetrasiloxane and the allylimine compound should be such that the amount of the siloxane is at least equimolar to or, preferably, at least 1.2 times by moles of the amount of the allylimine compound. The reaction is undertaken at a temperature in the range from 20° to 200° C. or, preferably, from 40° to 120° C.

The catalyst for the addition reaction is well known in the art and selected from those compounds of a metal belonging to the Eighth Group of the Periodic Table including platinum compounds such as chloroplatinic acid in the form of an alcohol solution or complex compounds with an aldehyde or an olefin, rhodium compounds and palladium compounds.

The inventive organocyclotetrasiloxane of the general formula (I) is reactive by virtue of the functional groups or linkages in a molecule susceptible to the addition reaction with an aliphatically unsaturated linkage or to the dehydrogenation reaction with a hydroxylamine compound. Accordingly, the compounds find uses as a crosslinking agent for a vinyl-containing organopolysiloxane as a principal ingredient of a silicone rubber or for a hydroxy-containing organopolysiloxane.

The organocyclotetrasiloxane compounds of the formula (I) in which Y is a disubstituted aminoxy group are themselves novel compounds not known nor described in any prior art literatures and are obtained by the above mentioned dehydrogenation reaction between a hydroxylamine compound of the formula $R^2{}_2NOH$ and the cyclotetrasiloxane compound of the formula (I) in which Y is a hydrogen atom in the presence of a catalyst which may be the same one as used in the addition reaction of the allylimine compound and the organopolysiloxane containing Si-H linkages. The amount of the hydroxylamine compound used in the dehydrogenation reaction should be at least equimolar to the Si-H linkages in the siloxane compound and the reaction is carried out at a temperature in the range from −20° to +150° C. or, preferably, from 0° to 80° C.

The inventive organocyclotetrasiloxanes containing the disubstituted aminoxy groups are also useful as a crosslinking agent for a silicone rubber mainly composed of a diorganopolysiloxane terminated at the molecular chain ends with hydroxy groups or a coupling agent therefor so that they can find wide applications in the fields of sealing materials, electric insulating materials, rubbery elastomers and the like. In particular, the silicone rubber composition formulated with this inventive cyclotetrasiloxane compound in which Y is a disubstituted aminoxy group is advantageous in a strong adhesive bonding exhibited in curing to the surface of a variety of substrate materials without the use of a primer.

Following are the examples to illustrate the inventive novel compounds in further detail.

EXAMPLE 1

Isopropylideneallylimine of the formula $Me_2C=N-CH_2-CH=CH_2$ was prepared by the reaction of 500 g (8.61 moles) of acetone and 500 g (8.76 moles) of allylamine in the presence of 5 g of concentrated hydrochloric acid. Thus, the allylamine was added dropwise into the acetone over a period of 1 hour, upon which the temperature of the reaction mixture was increased to about 50° C., where agitation was further continued for additional two hours. After the end of the reaction, the mixture was dehydrated by adding 60 g of sodium hydroxide followed by distillation of the upper layer separated from the mixture to give 452 g of the desired isopropylideneallylimine boiling at 56° C. under a pressure of 100 mmHg. The yield was about 54% of the theoretical value.

Into a reaction vessel were introduced 601 g (10 moles) of 1,3,5,7-tetramethylcyclotetrasiloxane, 600 g of toluene and 0.34 g of an isopropyl alcohol solution of chloroplatinic acid in a concentration of 2% by weight as platinum and 162 g (1.67 moles) of the above prepared isopropylideneallylimine were added dropwise into the reaction mixture kept at 80° C. over a period of 1 hour and agitation was further continued for additional one hour at the same temperature.

The reaction mixture thus obtained was subjected to distillation under reduced pressure to give 309.6 g of a clear, colorless liquid boiling at 112° C. under a pressure of 3 mmHg. The undermentioned results of the analyses of this product indicated that it was an organocyclotetrasiloxane of the formula (I) in which Y is a hydrogen atom and X is a group expressed by the formula $Me_2C=N-CH_2CH_2CH_2-$. The above given yield of the product was about 55% of the theoretical value.

| Elementary analysis: | | |
|---|---|---|
| | Calculated as $C_{10}H_{27}O_4NSi_4$, % | Found, % |
| C | 35.57 | 35.62 |
| H | 8.06 | 8.03 |
| Si | 33.27 | 33.23 |
| Molecular weight by mass spectrometry: | | |
| Found | | 337 |
| Calculated as $C_{10}H_{27}O_4NSi_4$ | | 337 |
| Hydrogen evolution by alkali decomposition: (at N.T.P.) | | |
| Found | | 201 ml/g |
| Calculated | | 199 ml/g |
| Refractive index $n_D{}^{25}$: | | 1.4326 |
| Infrared absorption spectrum: (see FIG. 1) | | |

EXAMPLE 2

The reaction procedure was substantially the same as in Example 1 except that the isopropylideneallylimine was replaced with 209 g of (1-ethylpropylidene)allylimine obtained in a similar manner to isopropylideneallylimine by use of diethylketone instead of acetone. Distillation of the reaction mixture under reduced pressure yielded 340 g of a fraction of a clear, colorless liquid boiling at 115° to 118° C. under a pressure of 6 mmHg. The results of the analyses undertaken with this product indicated that it was an organocyclotetrasiloxane of the formula (I) in which Y is a hydrogen atom and X is a group expressed by the formula $Et_2C=N-CH_2CH_2CH_2-$. The above given yield of the product was about 55.8% of the theoretical value.

| Elementary analysis: | | |
|---|---|---|
| | Calculated as $C_{12}H_{31}O_4NSi_4$, % | Found, % |
| C | 39.45 | 39.39 |
| H | 8.54 | 8.53 |
| Si | 30.72 | 30.78 |
| Molecular weight by mass spectrometry: | | |
| Found | | 365 |

-continued

Figure 2:
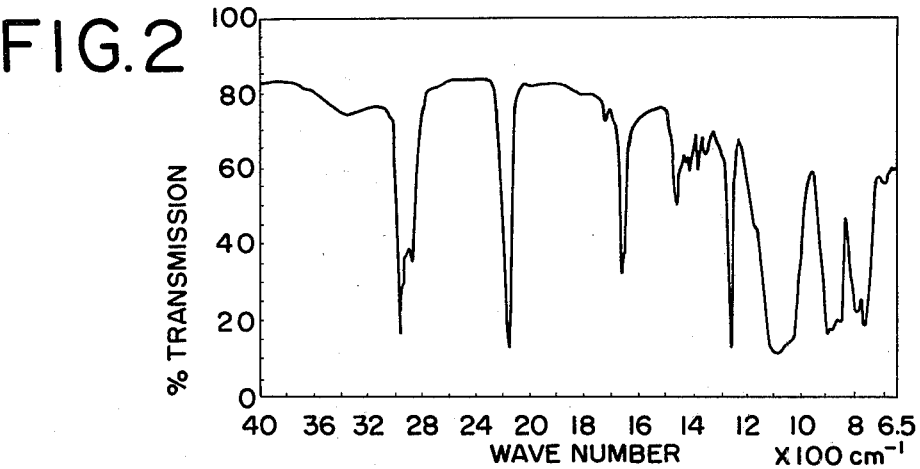

| Calculated as $C_{12}H_{31}O_4NSi_4$ | 365 |
|---|---|
| Hydrogen evolution by alkali decomposition: (at N.T.P.) | |
| Found | 183 ml/g |
| Calculated | 184 ml/g |
| Refractive index $N_D^{25}$: | 1.4343 |
| Infrared absorption spectrum: (see FIG. 2) | |

EXAMPLE 3

The reaction procedure was substantially the same as in Example 1 except that the isopropylideneallylimine was replaced with 186 g of sec-butylideneallylimine obtained in a similar manner to isopropylideneallylimine by use of methylethylketone in place of acetone. Distillation of the reaction mixture under reduced pressure yielded 360 g of a fraction of a clear, colorless liquid boiling at 109° to 110° C. under a pressure of 4 mmHg. The undermentioned results of the analyses undertaken with this product indicated that it was an organocyclotetrasiloxane of the formula (I) in which Y is a hydrogen atom and X is a group expressed by the formula

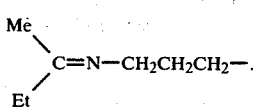

The above given yield of the product was about 61.4% of the theoretical value.

Elementary analysis:

| | Calculated as $C_{11}H_{29}O_4NSi_4$, % | Found, % |
|---|---|---|
| C | 37.57 | 37.51 |
| H | 8.31 | 8.37 |
| Si | 31.95 | 31.93 |

Molecular weight by mass spectrometry:

| Found | 351 |
|---|---|
| Calculated as $C_{11}H_{29}O_4NSi_4$ | 351 |
| Hydrogen evolution by alkali decomposition: (at N.T.P.) | |
| Found | 193 ml/g |
| Calculated | 191 ml/g |
| Refractive index $n_D^{25}$: | 1.3432 |
| Infrared absorption spectrum: | |

2350 cm$^{-1}$ for $\diagdown$Si—H and 1660 cm$^{-1}$ for =C=N—

EXAMPLE 4

The experimental procedure was substantially the same as in Example 1 except that the isopropylideneallylimine was replaced with 229 g of cyclohexylideneallylimine of the formula

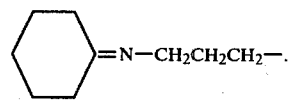

obtained in a similar manner to isopropylideneallylimine by use of cyclohexanone in place of acetone. Distillation of the reaction mixture under reduced pressure gave 580 g of a clear, pale yellow liquid. The undermentioned results of the analyses undertaken with this product indicated that it was an organocyclotetrasiloxane of the formula (I) in which Y is a hydrogen atom and X is a group expressed by the formula

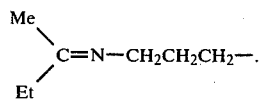

The above given yield of the product was about 92% of the theoretical value.

Elementary analysis:

| | Calculated as $C_{13}H_{31}O_4NSi_4$, % | Found, % |
|---|---|---|
| C | 41.35 | 41.42 |
| H | 8.28 | 8.20 |
| Si | 29.76 | 29.85 |

Molecular weight by mass spectrometry:

| Found | 377 |
|---|---|
| Calculated as $C_{13}H_{31}O_4NSi_4$ | 377 |
| Hydrogen evolution by alkali decomposition: (at N.T.P.) | |
| Found | 178 ml/g |
| Calculated | 175 ml/g |
| Infrared absorption spectrum: | |

2350 cm$^{-1}$ for $\diagdown$Si—H and 1660 cm$^{-1}$ for =C=N—

EXAMPLE 5

Into a reaction vessel were taken 351 g (1.0 mole) of the organocyclotetrasiloxane obtained in Example 3 above and 321 g (3.6 moles) of diethylhydroxylamine were added dropwise thereinto at room temperature over a period of 2 hours in an atmosphere of nitrogen followed by gradual temperature elevation up to 60° C. where the reaction was further continued for additional 1 hour.

The reaction mixture after completion of the reaction was subjected to stripping of volatile matter under a reduced pressure at 60° C. to leave 600 g of a clear, pale yellow liquid having a viscosity of 60 centistokes at 25° C. The undermentioned results of the analyses undertaken with this product indicated that the product is an organocyclotetrasiloxane of the formula (I) in which Y is a diethylaminoxy group and X is a group expressed by the formula

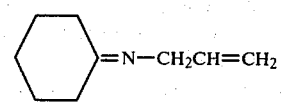

The above given yield of the product was about 98% of the theoretical value.

Elementary analysis:

| | Calculated as $C_{23}H_{56}O_7N_4Si_4$, % | Found, % |
|---|---|---|
| C | 44.82 | 44.89 |
| H | 9.16 | 9.22 |
| N | 9.09 | 9.03 |
| Si | 18.23 | 18.18 |

Figure 3:
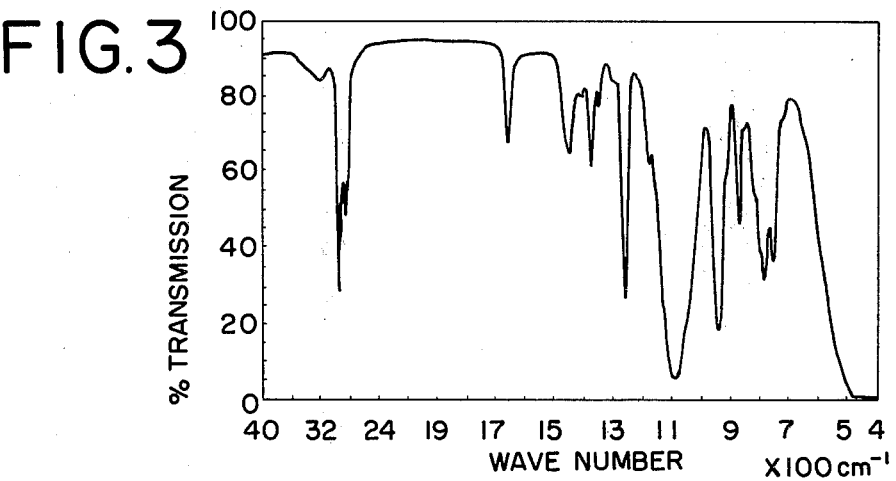

Molecular weight by mass spectrometry:

| | |
|---|---|
| Found | 612 |
| Calculated as $C_{23}H_{56}O_7N_4Si_4$ | 612 |
| Infrared absorption spectrum: (see FIG. 3) | |

EXAMPLE 6

The experimental procedure was substantially the same as in Example 5 above except that the starting organocyclotetrasiloxane was the compound obtained in Example 1 in an amount of 337 g (1.0 mole) in place of the compound obtained in Example 3. Stripping of the reaction mixture gave 580 g of a clear, pale yellow liquid which was identified by the undermentioned analytical results to be the organocyclotetrasiloxane of the formula (I) in which Y is a diethylaminoxy group and X is a 3-isopropylideneiminopropyl group. The above given yield of the product was about 96% of the theoretical value.

Elementary analysis:

| | Calculated as $C_{22}H_{54}O_7N_4Si_4$, % | Found, % |
|---|---|---|
| C | 43.95 | 44.02 |
| H | 9.05 | 9.12 |
| N | 9.31 | 9.25 |
| Si | 18.69 | 18.60 |

| Molecular weight by mass spectrometry: | |
|---|---|
| Found | 598 |
| Calculated as $C_{22}H_{54}O_7N_4Si_4$ | 598 |

EXAMPLE 7

The experimental procedure was substantially the same as in Example 5 except that the starting organocyclotetrasiloxane was the compound obtained in Example 2 in an amount of 365 g (1.0 mole) in place of the compound obtained in Example 3. The resultant product was a clear, pale yellow liquid in an amount of 610 g, which was identified by the undermentioned analytical results to be the organocyclotetrasiloxane of the formula (I) in which Y is a diethylaminoxy group and X is a group expressed by the formula $Et_2C=N-CH_2CH_2CH_2-$. The above given yield of the product was about 97% of the theoretical value.

Elementary analysis:

| | Calculated as $C_{24}H_{58}O_7N_4Si_4$, % | Found, % |
|---|---|---|
| C | 45.81 | 45.90 |
| H | 9.29 | 9.24 |
| N | 8.90 | 8.94 |

| Molecular weight by mass spectrometry: | |
|---|---|
| Found | 626 |
| Calculated as $C_{24}H_{58}O_7N_4Si_4$ | 626 |

EXAMPLE 8

The experimental procedure was substantially the same as in Example 5 except that the starting organocyclotetrasiloxane was the compound obtained in Example 4 in an amount of 378 g (1.0 mole) in place of the compound obtained in Example 2. The resultant product was a clear, pale yellow liquid in an amount of 605 g, which was identified by the undermentioned analytical results to be the organocyclotetrasiloxane of the formula (I) in which Y is a diethylaminoxy group and X is a group expressed by the formula

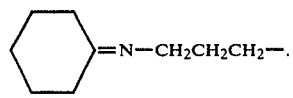

The above given yield of the product was about 95% of the theoretical value.

Elementary analysis:

| | Calculated as $C_{25}H_{58}O_7N_4Si_4$, % | Found, % |
|---|---|---|
| C | 16.98 | 17.02 |
| H | 9.15 | 9.20 |
| N | 8.76 | 8.71 |

| Molecular weight by mass spectrometry: | |
|---|---|
| Found | 638 |
| Calculated as $C_{25}H_{58}O_7N_4Si_4$ | 638 |

What is claimed is:

1. An organocyclotetrasiloxane represented by the general formula

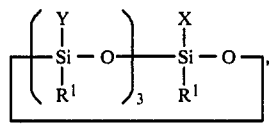

in which Y is a hydrogen atom or a disubstituted aminoxy group of the formula $R^2_2N-O-$, $R^2$ being a monovalent hydrocarbon group having from 1 to 6 carbon atoms, X is a hydrocarbylideneimino-substituted propyl group of the formula

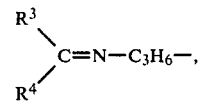

$R^3$ being a monovalent hydrocarbon group free from aliphatic unsaturation having from 1 to 8 carbon atoms and $R^4$ being a hydrogen atom or a monovalent hydrocarbon group free from aliphatic unsaturation having from 1 to 8 carbon atoms, or of the formula

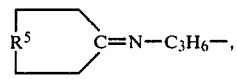

$R^5$ being a divalent hydrocarbon group free from aliphatic unsaturation having from 4 to 8 carbon atoms, and $R^1$ is a monovalent hydrocarbon group having from 1 to 8 carbon atoms.

2. The organocyclotetrasiloxane as claimed in claim 1 wherein Y is a hydrogen atom.

3. The organocyclotetrasiloxane as claimed in claim 1 wherein Y is a disubstituted aminoxy group.

4. The organocyclotetrasiloxane as claimed in claim 2 wherein $R^1$ is a methyl group, and $R^3$ and $R^4$ are each a methyl group.

5. The organocyclotetrasiloxane as claimed in claim 1 wherein $R^1$ is a methyl group and $R^3$ and $R^4$ are each an ethyl group.

6. The organocyclotetrasiloxane as claimed in claim 2 wherein $R^1$ is a methyl group, $R^3$ is a methyl group and $R^4$ is an ethyl group.

7. The organocyclotetrasiloxane as claimed in claim 2 wherein $R^1$ is a methyl group and $R^5$ is a pentamethylene group.

8. The organocyclotetrasiloxane as claimed in claim 3 wherein $R^1$ is a methyl group, $R^2$ is an ethyl group, $R^3$ is a methyl group and $R^4$ is an ethyl group.

9. The organocyclotetrasiloxane as claimed in claim 3 wherein $R^1$ is a methyl group, $R^2$ is an ethyl group, and $R^3$ and $R^4$ are each a methyl group.

10. The organocyclotetrasiloxane as claimed in claim 3 wherein $R^1$ is a methyl group, $R^2$ is an ethyl group and $R^3$ and $R^4$ are each an ethyl group.

11. The organocyclotetrasiloxane as claimed in claim 3 wherein $R^1$ is a methyl group, $R^2$ is an ethyl group and $R^5$ is a pentamethylene group.

* * * * *